United States Patent
Albrod et al.

(10) Patent No.: US 6,555,730 B1
(45) Date of Patent: Apr. 29, 2003

(54) SUPPORTING MATERIAL FOR MEDICAL PURPOSES

(75) Inventors: Andreas Albrod, Seevetal (DE); Frank Ganschow, Elmshorn (DE); Peter Himmelsbach, Buxtehude (DE); Klaus Keite-Telgenbüscher, Hamburg (DE); Daniela Peeters-Bendix, Ellerbek (DE); Heidi Sacker, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/529,872

(22) PCT Filed: Oct. 21, 1998

(86) PCT No.: PCT/EP98/06666

§ 371 (c)(1),
(2), (4) Date: Jul. 3, 2000

(87) PCT Pub. No.: WO99/21520

PCT Pub. Date: May 6, 1999

(30) Foreign Application Priority Data

Oct. 23, 1997 (DE) .......................................... 197 46 913

(51) Int. Cl.$^7$ .......................... A61F 13/00; A61L 15/07
(52) U.S. Cl. ........................... 602/58; 602/41; 602/45; 602/76; 442/269; 442/305; 428/317.9; 428/295.4; 428/297.4; 428/297.1; 428/902
(58) Field of Search ............................... 602/41–59, 76, 602/77; 442/269, 365, 304, 305, 370; 428/902, 304.4, 295.4, 297.4, 297.1, 317.9; 604/304

(56) References Cited

U.S. PATENT DOCUMENTS

| 4,668,563 A | | 5/1987 | Buese et al. |
| 4,773,238 A | | 9/1988 | Zafiroglu |
| 4,967,740 A | | 11/1990 | Riedel |
| 5,629,078 A | | 5/1997 | Ganschow |
| 6,074,965 A | * | 6/2000 | Bodenschatz et al. ...... 442/269 |

FOREIGN PATENT DOCUMENTS

| AU | 73555/74 | 1/1975 |
| DE | 571 244 | 5/1932 |
| DE | 94 01 037 | 4/1994 |
| DE | 42 37 252 A1 | 5/1994 |
| DE | 44 42 092 A1 | 5/1996 |
| DE | 44 42 093 A1 | 5/1996 |
| DE | 44 42 507 A1 | 6/1996 |
| DE | 195 31 291 A1 | 2/1997 |
| DE | 196 31 422 A1 | 2/1998 |

* cited by examiner

*Primary Examiner*—Kim M. Lewis
(74) *Attorney, Agent, or Firm*—Norris McLaughlin & Marcus

(57) ABSTRACT

The invention relates to the use of a non-woven fabric which is over-stitched by means of stitching threads as a supporting material for medical purposes. The invention is characterized in that the maximum tensile force of supporting material is equal to at least 30 N/cm and at least one side of the supporting material is partially or completely coated with a self-adhesive mass.

54 Claims, No Drawings

SUPPORTING MATERIAL FOR MEDICAL PURPOSES

BACKGROUND OF THE INVENTION

1. Field of the Invention

The invention relates to a backing material for medical purposes, preferably for orthopaedic dressings and bandages, which is coated on at least one side completely or partially with a selfadhesive composition.

2. The Related Art

As backing materials for medical purposes, numerous materials based on films, wovens, knits, nonwovens, gels or foams have already been disclosed and are also. employed in practice. The materials, which are often coated with a self-adhesive composition as well, are required to be skin-compatible, generally permeable to air and water vapour, and also easy to model and conformable. Based on these requirements, a very thin or soft backing is frequently preferred. For handling and in use, however, the backing materials are also required to be of sufficient strength and possibly of limited extensibility. Furthermore, the backing material should retain sufficient strength and low extensibility even after becoming wet through.

Thin backings, especially those made of nonwovens, are highly permeable to air and water vapour. For certain applications, however, their strength is too low and their elongation too high.

Specific applications, an example being tapes for functional tape dressings for the prophylaxis and therapy of injuries, disorders and altered states of the musculoskeletal system, require inelastic backings having high strength in the direction of stress. This is achieved by using woven-fabric backings, usually of cotton or viscose. Backing materials of this kind, with appropriately high basis weight, are generally cost-intensive. High conformability and modelability can only be achieved by means of a woven fabric of relatively low strength. When such a fabric is stressed, however, it generally exhibits a degree of elongation, which is undesirable for its use.

When the dressings listed become wet through, they generally lose strength or become more extensible. This is likewise undesirable for their use and has to date been compensated by more frequent changing of dressings, which, however, is cost-intensive.

Lamination with reinforcement threads has also been disclosed in the prior art by German Patent 571 244, although the reinforcement threads employed therein are not of high tenacity. The document, then, generally gives no indication of an inelastic backing.

In addition, AU 73555/74 describes by way of example a glass filament-reinforced backing material for medical application based on foam.

U.S. Pat. No. 4,668,563 describes a glass fibre-reinforced material which, however, is elastic. All backing materials mentioned, however, are not reinforced by stitching.

DE 44 42 092 and DE U 94 01 037 describe adhesive tapes based on stitchbonded webs which are partially coated on the reverse side of the backing. Such adhesive tapes are used preferably in cable bandaging.

DE 44 42 093 is also based on the use of a nonwoven as backing for an adhesive tape; in this case, a cross-laid fibre web is described which is reinforced by the formation of loops from the fibres of the web. DE 44 42 507 likewise discloses an adhesive tape for cable bandaging, but bases it on so-called Kunit or Multikunit webs.

A utility or special suitability of these backing materials for medical purposes, however, cannot be inferred from the documents cited. In particular, the publications give indications neither of sufficient skin compatibility of the adhesive compositions nor of functionally secured bonding on the skin or an advantageous permeability to air and water vapour.

U.S. Pat. No. 4,773,238 describes a fibre web with lengthwise overstitching, the stitching seams being intended to amount to no more than 20% by weight based on the weight of the total nonwoven. Proposed in accordance with the invention is the utility as an insert for filters in dust filtration.

U.S. Pat. No. 4,967,740 gives a general disclosure of backing materials for use in medical supply, which are produced in a one-step process. In this process, the backing is impregnated simultaneously with an elastomer and with a release solution. In this way, the material can be presented without release paper on a roll.

In a listing of a large number of appropriate backings, mention is made, inter alia, of overstitched nonwovens, without the skilled worker being given any indication as to how the nonwoven should, specifically, be configured in order to meet the requirements placed on a medical backing.

Highly adhesive orthopaedic bandages and other medical products are usually coated over the whole of their area with a rubber adhesive composition. These adhesive compositions then permit a high bond strength on the reverse face of the backing, which ensures a stable functional dressing in the case of systems of circularly applied dressings with a plurality of plies.

The object of the invention was to provide a nonwoven-based backing material which is suitable for medical requirements and does not have the disadvantages known from the prior art. These inventions and other objects of the invention are achieved by the invention described herein.

SUMMARY OF THE INVENTION

Accordingly, a nonwoven overstitched by means of yarns is used as backing material for medical purposes, the number of stitches on the nonwoven being advantageously at least 5/cm, preferably from 7/cm to 50/cm. The ultimate tensile stress strength of the backing material is at least 30 N/cm, preferably from 40 to 450 N/cm, with particular preference from 50 to 250 N/cm, and the backing material is coated partially or over its full area on at least one side with a self-adhesive composition.

The yarns preferably have a water absorption of less than 30%, with particular preference less than 20%. The water absorption can be regenerated by the atmospheric humidity.

DETAILED DESCRIPTION OF THE INVENTION

Accordingly, materials which can be used for the yarns are, advantageously, polymeric fibres made from polypropylene, polyester, polyamide, aramid or polyethylene, and also mineral fibres such as glass fibres or carbon fibres. In addition it is also possible to use multi-strand yarns or mixed multistrands, especially Sirospun yarns. For specific applications, single- or multi-strand fibre blend yarns may also be employed. Furthermore, the yarns can have been at least partly coloured in order to make the backing material more visually appealing.

For specific applications, the yarn can also be elastic. From this there is then regenerated an elastic base support having an elongation of up to 250% at a load of 10 N/cm. Mention may be made here, for example, as a polyamide yarn (Lycra®, DuPont) [sic]. A backing material of this kind generates a compression force of from 0.2 N/cm to 10 N/cm at an elongation of from 20% to 70% and is used in compression technology.

In the case of the alternative embodiment of the subject-matter of the invention, a nonwoven is used as backing material for medical purposes. In this case, the nonwoven is reinforced by the formation of stitches formed by loops from the fibres of the web, the number of stitches on the web being advantageously at least 5/cm, preferably from 7/cm to 50/cm. The ultimate tensile stress strength of the backing material is at least 30 N/cm, preferably from 40 to 450 N/cm, with particular preference from 50 to 250 N/cm, and the backing material is coated partially or over its full area on at least one side with a self-adhesive composition.

The backing materials are based on known nonwovens which are mechanically consolidated either by overstitching with separate yarns or by looping. In the first case, the resulting structures are the web-yarn stitchbonds. For their production, a fibre web is taken, which can, for example, be in cross-plating configuration, and is overstitched with separate yarns in pillarstitch formation or tricot formation.

These nonwovens are known by the name "Maliwatt" (from the company Malimo) or Arachne.

With the second type of consolidation, again, preferably a cross-plated web is taken. In the course of the consolidation operation, needles draw out fibres from the web itself and form them into loops, with stitches being formed in pillarstitch formation. This web stitchbond is in circulation under the name "Malivlies" [Mali Fleece], again from the company Malimo.

An overview of the various kinds of mechanically consolidated fibre nonwovens can be found in the article "Kaschierung von Autopolsterstoffen mit Faservliesen" [Laminating car upholstery materials with fibre webs] by G. Schmidt, Melliand Textilberichte 6/1992, pages 479 to 486.

Advantageously, the webs have longitudinal stitches, in which case the orientation of the yarns ought to be aligned in accordance with the stresses on the backing material in use.

Starting materials which can be used for the nonwoven material are generally all organic and inorganic, natural- and synthetic-based fibre materials. Examples that may be mentioned include viscose, cotton, silk, polypropylene, polyester, polyamide, aramid or polyethylene, and also mineral fibres such as glass fibres or carbon fibres. The present invention is, however, not restricted to the said materials; rather, it is possible to use a large number of other fibres for web formation.

The fibres used to form the web preferably have a water retention capacity of more than 0.5%, preferably between 2 to [sic] 70%, with particular preference between 3 and 50%.

In one preferred embodiment, the backing material has an ultimate tensile stress elongation of less than 40%, preferably less than 15%, with particular preference less than 10%.

For a web overstitched with yarns, this is achieved firstly by the use of a yarn material having a higher modulus of elasticity and secondly with the use of stitching which ensures a yarn position which is stretched as much as possible.

Advantageous combinations of material are, for example, yarns of high-strength polymer fibres such as polyamide, polyester, highly stretched polyethylene, or mineral fibres such as glass, and initial web materials such as cotton or staple viscose rayon.

For a web in which the formation of stitches takes place by the loops being formed from the fibres of the web, the material of the initial web should be selected accordingly; corresponding comments apply to the stitching.

It has also been found advantageous for the backing material to have a basis weight of less than 350 g/m$^2$, preferably from 10 to 180 g/m$^2$.

In one further advantageous embodiment, the backing material can be torn by hand perpendicular to the orientation of the stitches and/or in the direction of the stitches.

Furthermore, the backing material may have been reinforced with one or more monofil, multifil, staple fibre or spun fibre yarns and/or with oriented high-strength fibres, the yarns and/or fibres having in particular a strength of at least 40 cN/tex. In addition it is also possible to employ multi-strand yarns or mixed multistrands, especially Sirospun yarns. For specific applications, single- or multi-strand fibre blend yarns may also be employed. These may comprise, for example, core-spun yarns or special staple fibre core-spun yarns. An advantage here is that by combining different fibre types it is possible to achieve particular properties or specific properties in the reinforcement thread. Examples of this are the combinations of polyester or polyamide with cotton or staple viscose rayon.

The reinforcement fibres or filaments here can consist of organic or inorganic materials: for example, and preferably, glass, carbon, polyester or specific polyamides, and the reinforcement fibres may also have been at least partly coloured in order to render the backing material more visually appealing. In this way it is readily possible to differentiate visually the reinforced backing. Coloured glass or polymer filaments are particularly suitable for this purpose.

In one advantageous embodiment the backing material attains through the addition of high-strength fibres or filaments an ultimate tensile stress strength of more than 60 cN/tex, an ultimate tensile stress strength of more than 50 N/cm and an ultimate tensile stress elongation of less than 25% with a basis weight of less than 140 g/m$^2$. A backing material of this kind is particularly suitable for acting as the backing for a tape strip.

The number of attached or introduced filaments or high-strength fibres depends primarily on the particular intended use and on the desired ultimate tensile stress strength and ultimate tensile stress elongation of the backing material, on its inherent nature and on the respective strength of the fibres and filaments themselves, and can therefore be varied within relatively wide limits.

Advantageous combinations of material are, for example, reinforcement filaments or fibres of high-strength polymer fibres such as polyamide, polyester, highly stretched polyethylene, or mineral fibres such as glass, and initial web materials such as cotton or staple viscose rayon.

In addition, the reinforcements are preferably inserted specifically in accordance with the direction of stress of the backing material, i.e. in the longitudinal direction. If more appropriate, however, they can also extend only or additionally in the transverse or oblique direction or, for example, in curved, spiral or zigzag formation, or randomly.

In one further advantageous embodiment, the backing material can be torn by hand perpendicular to the orientation of the reinforcement and/or in the direction of the reinforcement.

With greater strength of the nonwoven material and an increasing proportion of reinforcement fibres, the backing withstands greater stress and loading. Even very highly reinforced backing materials are able to absorb or allow the passage of large amounts of moisture, and hence provide a pleasant sensation for the user, with the reinforcements absorbing little or no moisture and so undergoing no change in their properties.

In the case of known ready-made tape dressings the reinforcement filaments or fibres are preferably arranged equally in accordance with the direction of stress in the applied state. Since these dressings have already been cut to size or punched out, tearability by hand is not a requirement here.

A backing of this kind which is suitable for tapes has, for example, an ultimate tensile stress strength of 50 N/cm and an ultimate tensile stress elongation of less than 20% for a basis weight of 200 g/m$^2$ or 250 g/m$^2$, respectively, using the self-adhesive composition.

For the coating, preference is given to a self-adhesive composition which has a high bond strength. For orthopaedic applications, especially, the adhesive composition ought to have a high initial tack.

As adhesive compositions it is possible with advantage to use self-adhesive compositions based on natural and synthetic rubbers and on other synthetic polymers such as acrylates, methacrylates, polyurethanes, polyolefins, polyvinyl derivatives, polyesters or silicones with corresponding additives such as tackifier resins, plasticizers, stabilizers and other auxiliaries where necessary.

Thermoplastic hot-melt adhesive compositions, in particular, have advantageous properties and are favoured for reasons concerned with the production process.

Their softening point should be higher than 50° C., since the application temperature in the case of the coating is generally at least 90° C., preferably between 120° C. and 150° C., or between 180° C. and 220° C. in the case of special adhesive compositions such as silicones. If desired, post crosslinking by means of high-energy radiation such as UV rays or electron beams may be applied.

Preferred hot-melted adhesive compositions based on block copolymers are notable for their diverse possibilities for variation, since the controlled reduction in the glass transition temperature of the self-adhesive composition as a result of the selection of the tackifiers, plasticizers, polymer molecule size and molecular distribution of the starting components ensures the required bonding to the skin in a manner appropriate to their function, even at critical points of the human locomotor system.

The high shear strength of the hot-melt adhesive composition is achieved through the high cohesiveness of the polymer. The good tack results from the range of tackifiers and plasticizers employed.

For especially strongly adhesive systems, the hot-melt adhesive composition is preferably based on block copolymers, especially A-B-, A-B-A block copolymers or mixtures thereof. The hard phase A is principally polystyrene or its derivatives and the soft phase B contains ethylene, propylene, butylene, butadiene, isoprene or mixtures thereof, particular preference being given here to ethylene and butylene or mixtures thereof.

Polystyrene blocks, however, may also be present in the soft phase B in amounts of up to 20%. The overall proportion of styrene should, however, always be less than 35% by weight. Preferably, styrene proportions of between 5% and 30% are preferred, since a relatively low proportion of styrene makes the adhesive composition more conformable.

The controlled blending of diblock and triblock copolymers is particularly advantageous, preference being given to a proportion of diblock Copolymers of less than 80% by weight.

In one advantageous embodiment the hot-melt adhesive composition has the following stated composition:

from 10% by weight to 90% by weight of block copolymers,
from 5% by weight to 80% by weight of tackifiers such as oils, waxes, resins and/or mixtures thereof, preferably mixtures of resins and oils,
less than 60% by weight of plasticizers,
less than 15% by weight of additives, and
less than 5% by weight of stabilizers.

The aliphatic or aromatic oils, waxes and resins used as tackifiers are preferably hydrocarbon oils, waxes and resins, the consistency of the oils, such as paraffinic hydrocarbon oils, or of the waxes, such as paraffinic hydrocarbon waxes, accounting for their favourable effect on bonding to the skin. Plasticizers used are medium-chain or long-chain fatty acids and/or their esters. These additions serve to establish the adhesion properties and the stability. If desired, further stabilizers and other auxiliaries are employed. Filling the adhesive composition with mineral or organic fillers, fibres or hollow or solid microbeads is possible.

The self-adhesive composition has a softening point of more than 70° C., preferably from 80° C. to 140° C.

The hot-melt self-adhesive compositions are preferably formulated so that at a frequency of 0.1 rad/s they have a dynamic-complex glass transition temperature of less than 5° C., preferably from –3 °C. to –30° C., with very particular preference from –9° C. to –25° C.

Stringent requirements are placed in terms of the adhesion properties on medical backing materials. For ideal use the hot-melt adhesive composition should possess a high tack. There should be functionally appropriate bond strength to the skin and to the reverse of the backing. So that there is no slipping, the hot-melt adhesive composition is also required to have a high shear strength. By the controlled reduction in the glass transition temperature of the adhesive composition, which is a result of the selection of the tackifiers, the plasticizers, the polymer molecule size and the molecular distribution of the starting components, the required, functionally appropriate bonding to the skin and to the reverse of the backing is achieved. The high shear strength of the adhesive composition which is employed here is obtained by virtue of the high cohesiveness of the block copolymer. The good tack is the result of the range of tackifiers and plasticizers employed.

Product properties such as tack, glass transition temperature and shear stability can be quantified readily using a dynamo-mechanical frequency measurement. In this case, use is made of a rheometer controlled by shearing stress. The results of this measurement method give information of the physical properties of a substance by taking into account the viscoelastic component. In this instance, at a predetermined temperature, the self-adhesive composition is set in oscillation between two plane-parallel plates at variable frequencies and with low deformation (linear viscoelastic region). Via a pickup control unit, with computer assistance, the quotient ($Q = \tan \delta$) between the loss modulus (G", viscous component) and the storage modulus (G', elastic component) is determined.

$$Q = \tan \delta = G''/G'$$

A high frequency is chosen for the subjective sensing of the tack, and a low frequency for the shear strength.

The glass transition temperature is the temperature at which amorphous or partially crystalline polymers undergo transition from the liquid or rubber-elastic state to the hard-elastic or glassy state, or vice versa (Rompp Chemie-Lexikon, 9th Ed., Volume 2, page 1587, Georg Thieme Verlag Stuttgart—New York, 1990). It corresponds to the maximum of the temperature function at a predetermined frequency. For medical applications in particular, a relatively low glass transition point is required.

| Designation | $T_g$ low frequency | Conformability low frequency/RT | Tack high frequency/RT |
|---|---|---|---|
| Hot-melt adhesive composition A | $-10 \pm 2°$ C. | $\tan \delta\ 0.35 \pm 0.05$ | $\tan \delta = 1.70 \pm 0.10$ |
| Hot-melt adhesive composition B | $-9 \pm 2°$ C. | $\tan \delta = 0.22 \pm 0.03$ | $\tan \delta = 1.00 \pm 0.03$ |

Preference is given in accordance with the invention to self-adhesive compositions for which the ratio of the viscous component to the elastic component at a frequency of 100 rad/s and at 25° C. is greater than 0.7, or to self-adhesive compositions for which the ratio of the viscous component to the elastic component at a frequency of 0.1 rad/s at 25° C. is less than 0.4, preferably from 0.35 to 0.02 and, with very particular preference, between 0.3 and 0.1.

It is also advantageous, especially with use for medical products, if the adhesive composition is applied partially to the backing material, for example by means of halftone printing, screen printing, thermoflex printing or intaglio printing, because backing materials which have been adhesively treated in a continuous applied line may, under unfavourable circumstances, on application, induce mechanical irritations of the skin and are generally impermeable to air and water vapour.

Preference is given to application in the form of polygeometric domes and, especially, domes where the ratio of diameter to height is less than 5:1. Printed application of other forms and patterns on the backing material is also possible—for example, a printed image in the form of alphanumeric character combinations or patterns such as matrices, stripes and zigzag lines. The adhesive composition can be distributed uniformly over the backing material; alternatively, it can be applied with a thickness or density which varies over the area, as is appropriate for the function of the product.

The principle of thermal screen printing consists in the use of a rotating, heated, seamless, drum-shaped, perforated, cylindrical screen which is fed via a nozzle with the preferred hot-melt self-adhesive composition. A specially shaped nozzle lip (circular or square bar) presses the hot-melt adhesive composition, which is fed in via a channel, through the perforation of the screen wall and onto the backing web that is conveyed past it. This web is guided by means of a counterpressure roller against the external jacket of the heated screen drum at a rate which corresponds to the peripheral speed of the rotating screen drum.

In this context, the formation of the small domes of adhesive takes place by the following mechanism:

The pressure of the nozzle bar conveys the hot-melt adhesive composition through the screen perforation onto the backing material. The size of the domes formed is determined by the diameter of the screen perforation. The screen is lifted from the backing in accordance with the rate of transportation of the backing web (rotary speed of the screen drum). As a consequence of the high adhesion of the adhesive composition and the internal cohesion of the hot-melt, the limited supply of hot-melt adhesive composition in the perforations is drawn in sharp definition from the base of the dome that is already adhering to the backing and is conveyed by the pressure of the bar onto the backing. After the end of this transportation, the more or less strongly curved surface of the dome forms over the pre-defined base area in dependence on the rheology of the hot-melt adhesive composition. The height-to-base ratio of the dome depends on the ratio of the performation diameter to the wall thickness of the screen drum and on the physical properties (flow behaviour, surface tension and contact angle on the backing material) of the self-adhesive composition.

For the screen in thermal screen printing, the web-to-hole ratio can be less than 3:1, preferably less than or equal to 1:1, and in particular equal to 1:3.

The above-described mechanism of formation of the domes preferentially requires backing materials that are absorbent or at least wettable by hot-melt adhesive compositions. Non-wetting backing surfaces must be pretreated by chemical or physical techniques. This can be effected by additional measures such as corona discharge, for example, or by coating with substances which improve wetting.

Using the printing technique indicated it is possible to lay down the size and shape of the domes in a defined manner. The bond strength values which are relevant for use and which determine the quality of the products formed are within very narrow tolerances in the case of proper coating. The base diameter of the domes can be chosen from 10 to 5000 $\mu$m, the height of the domes from 20 to about 2000 $\mu$m, preferably from 50 to 1000 $\mu$m, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with various backing materials and applications.

The backing material is preferably coated at a rate of more than 2 m/min, preferably from 20 to 200 m/min, the chosen coating temperature being greater than the softening temperature.

The self-adhesive composition can be applied to the backing material at a weight per unit area of greater than 15 g/m$^2$, preferably between 90 g/m$^2$ and 400 g/m$^2$, with very particular preference between 130 g/m$^2$ and 300 g/m$^2$.

The percentage of the area that is coated with the self-adhesive composition should be at least 20% and can range up to approximately 95%, for specific products preferably from 40% to 60% and from 70% to 95%. This can be achieved, if appropriate, by multiple application, in which case it is also possible, if desired, to use self-adhesive compositions having different properties.

The combination of the preferred hot-melt adhesive composition and the preferred partial coating on the one hand ensures reliable bonding of the medical product to the skin and, on the other hand, allergic or mechanical skin irritations, at least which are visually perceptible, are ruled out, even in the case of use extending over a number of days.

The epilation of corresponding body regions and the transfer of composition to the skin are negligible owing to the high cohesiveness of the adhesive, since the adhesive does not attach to the skin and hair; rather, the anchorage of the adhesive composition to the backing material, at up to 12 N/cm (sample width), is good for medical applications.

Because of the intended breakage points that have been formed in the coating, layers of skin are no longer displaced with one another or against one another in the course of detachment. The non-displacement of these layers of skin and the relatively low level of epilation lead to an unprecedented degree of painlessness in such strongly adhering systems. In addition, the individual biomechanical control of bond strength, which exhibits a demonstrable reduction in the bond strength of these plasters, assists detachability. The applied backing material shows good proprioceptive effects.

Depending on the backing material and its temperature sensitivity, the hot-melt adhesive composition can be applied directly or can be applied first to an auxiliary support and then to the ultimate backing. In addition, subsequent calendering of the coated product and/or pretreatment of the backing, such as corona irradiation, may be advantageous for better anchorage of the adhesive film.

In addition, treatment of the hot-melt adhesive composition with an electron beam postcrosslinking, or a UV irradiation, may result in an improvement in the desired properties.

In a further advantageous embodiment, the self-adhesive compositions are foamed before being applied to the backing material.

In this case the self-adhesive compositions are preferably foamed using inert gases such as nitrogen, carbon dioxide, noble gases, hydrocarbons or air, or mixtures thereof. In many cases, foaming additionally by thermal decomposition of gas-evolving substances, such as azo, carbonate and hydrazide compounds, has been found to be suitable.

The degree of foaming, i.e. the gas content, should be at least about 5% by volume and can range up to about 85% by volume. In practice, levels of from 10% by volume to 75% by volume, preferably 50% by volume, have been found to be appropriate. Operating at relatively high temperatures of approximately 100° C. and with a comparatively high internal pressure produces very open-pored adhesive foam layers which are particularly permeable to air and water vapour. The advantageous properties of the foamed self-adhesive coatings, such as low consumption of adhesive, high tack and good conformity, even on uneven surfaces, owing to the elasticity and plasticity, and also the initial tack, can be utilized to best effect, very particularly, in the field of medical products.

The use of breathable coatings in conjunction with elastic and likewise breathable backing materials produces a level of wear comfort which is perceived subjectively by the user as being more pleasant.

A particularly suitable method of preparing the foamed self-adhesive composition operates by the foam mixing system. In this system, the thermoplastic self-adhesive composition is reactive with the intended gases such as, for example, nitrogen, air or carbon dioxide in various volume proportions (from about 10% by volume to 80% by volume) in a stator/rotor system under high pressure and at a temperature above the softening point (approximately 120° C.). Whereas the gas entry pressure is greater than 100 bar, the mixing pressures between gas and thermoplastic in the system are from 40 to 100 bar, preferably from 40 to 70 bar. The pressure-sensitive adhesive foam produced in this way can subsequently be passed through a line into the applicator unit. In the applicator unit, commercially customary nozzles, extruder systems or chamber systems are used.

By virtue of the foaming of the self-adhesive composition and the open pores in the composition which form as a result, and given the use of an inherently porous backing, the products coated with the adhesive composition have good permeability to water vapour and air. The amount of adhesive compositions required is considerably reduced without adverse effect on the adhesion properties. The adhesive compositions have a surprisingly good tack, since per gramme of composition there is more volume and thus more adhesion surface for wetting of the substrate that is to be bonded, and the plasticity of the adhesive compositions is increased by virtue of the foam structure. Anchoring to the backing material is also improved by this means. Moreover, the foamed adhesive coating, as already mentioned, gives the products a soft and conforming feel.

Foaming also generally reduces the viscosity of the adhesive compositions. This lowers the melt energy, and even thermally unstable backing materials can be coated directly.

The backing material coated with the adhesive composition can have an air permeability of greater than 1 $cm^3/(cm^{2*}s)$ preferably greater than 15 $cm^3/(cm^{2*}s)$, with very particular preference greater than 70 $cm^3/(cm^{2*}s)$, and also a water vapour permeability of greater than 500 $g/(m^{2*}24\ h)$, preferably greater than 1000 $g/(m^{2*}24\ h)$, with very particular preference greater than 2000 $g/(m^{2*}24\ h)$.

Furthermore, the backing material can also be provided with other finishes or treatments. These include, for example, corona, flame or plasma pretreatments, in order to increase the anchoring of the self-adhesive composition to the base web. In addition, the calendering of the backing material or of the web as yet untreated with pressure-sensitive self-adhesive composition, for the purpose of further consolidation and/or improvement in the anchoring of the pressure-sensitive self-adhesive composition, is an advantageous treatment.

In addition, on the side opposite to that coated with self-adhesive composition, the backing material can be finished with a water-repellent layer or impregnation which prevents rapid soaking on contact with water or perspiration. In addition to the known impregnations, this can also be done by the sewing-on of a sheet, advantageously a water vapour permeable sheet, by means of yarns directly during the consolidation of the web. The backing material can, furthermore, be finished with a release layer or impregnation and/or coating which reduces the bond strength of the self-adhesive composition. In this case as well, in addition to the known release materials, it is also possible to sew on a sheet, advantageously a water vapour permeable sheet, directly during the consolidation of the web.

Another procedure which has been found to be advantageous is the lamination of the web backing with at least one additional layer of foams or sheets, since by this means a combination of properties of particular type is obtained. A foam has a substantially higher damping quality than an unlaminated backing. Sheets can be used, for example, for sealing the surface.

Finally, following the coating operation, the backing material can be lined with a backing material which repels adhesive, such as siliconized paper, or can be provided with a wound pad or with padding.

Furthermore, the backing material can be coated with metallic substances by vapour deposition.

It is particularly advantageous for the backing material to be sterilizable, preferably by means of γ (gamma) radiation.

Particularly suitable for subsequent sterilization, therefore, are hot-melt adhesive compositions based on block copolymers which contain no double bonds. This applies in particular to styrene-butylene-ethylene-styrene block copolymers or styrene-butylene-styrene block copolymers. This procedure is not accompanied by any application-significant changes in the adhesive properties.

The backing material of the invention has a bond strength on the reverse side of the backing of at least 0.5 N/cm, in particular a bond strength of between 2.5 N/cm and 5 N/cm. Greater bond strengths may be achieved on other substrates.

The outstanding properties of the self-adhesively treated backing material according to the invention suggest its use for medical products, especially plasters, medical fixings, wound covers and also orthopaedic or phlebological bandages and dressings.

Advantageously it has been found that a reinforced backing material with such an adhesive coating, on becoming wet through—as is unavoidable, for example, in the course of water sports activities—has a stability which is better than that of customary commercial backing material. The relative increase in the ultimate tensile stress elongation of self-adhesively treated backing materials according to the invention after becoming wet through is only half as great as in the case of customary commercial self-adhesively treated backing materials.

By virtue of this the backing materials of the invention, which indeed are thus essentially inelastic, become useful for specific medical purposes, and it is also possible to employ backing materials whose use hitherto was impossible owing to lack of strength and/or excessive elongation.

With preference it is possible to use backing materials based on wovens, knits, nonwovens or composite products, provided they otherwise meet the requirements of medical use.

EXAMPLE

The text below describes by way of example a preferred backing material, without thereby wishing to restrict the invention unnecessarily.

The backing material used was a viscose-based nonwoven. The nonwoven was overstitched with a polyester yarn, the yarn count being 22/cm sample width. The water absorption of the polyester yarn was 0.3%. The backing material was calendered and impregnated. The resulting backing material had an ultimate tensile stress strength of about 50 N/cm and an ultimate tensile stress elongation of 28% in the lengthwise direction. The basis weight was 120 g/cm$^2$. Wetting the backing material completely was not possible owing to the choice of reinforcement materials. The backing material had an air permeability of 100 cm$^3$/(cm$^2$*s) and a water vapour permeability of greater than 2500 g/(m$^2$*24 h) and could be torn both partly and right through by hand in both crosswise and lengthwise directions. Overall, the backing material in the soaked-through state could be extended less than comparable backings which consisted only of cotton.

The hot-melt adhesive composition was applied to the backing by thermal screen printing.

The hot-melt adhesive composition was composed as follows:
- an A-B/A-B-A block copolymer, which consists of hard and soft segments, with a ratio of A-B-A to A-B of 2:1 and a styrene content in the polymer of 13 mol-%; its proportion in the adhesive composition is 40% by weight (Kraton G),
- a paraffinic hydrocarbon wax with a proportion in the adhesive composition of 52% by weight,
- hydrocarbon resins with a proportion of 7.5% by weight (Super Resin HC 140),
- an ageing inhibitor with a proportion of less than 0.5% by weight (Irganox).

The components employed were homogenized in a thermal mixer at 185° C. The glass transition by the abovementioned method was −9° C.

Direct coating took place at 50 m/min and at a temperature of 120° C. The backing material was partially coated with 120 g/m$^2$ using a 14 mesh screen with a thickness of 300 μm.

The bandage produced by this method exhibited reversible detachment from the skin and good permeability for air and water vapour. Owing to the high shear stability of the hot-melt pressure-sensitive adhesive, sufficiently [sic] stabilization and a good proprioreceptive effect were found. No skin irritations were observed, and the epilation observed following the removal of the bandage was negligible.

What is claimed is:

1. A backing material for medical purposes, comprised of a nonwoven overstitched by yarns, wherein the ultimate tensile stress strength of the backing material is at least 30 N/cm and the backing material is coated partially or over its full area on at least one side with a self-adhesive composition.

2. A backing material for medical purposes, comprised of a nonwoven web which is reinforced by the formation of stitches formed by loops from the fibers of the web, the number of stitches on the web being at least 5/cm, and wherein the ultimate tensile stress strength of the backing material is at least 30 N/cm, and the backing material is coated partially or over its full area on at least one side with a self-adhesive composition.

3. Backing material according to claim 1, wherein the number of stitches on the web is at least 5/cm.

4. Backing material according to claim 1 or 2, wherein the webs have longitudinal stitches.

5. Backing material according to claim 3 wherein the backing material generates a compression force of from 0.2 N/cm to 10 N/cm at an elongation of from 20% to 70%.

6. Backing material according to claim 1 or 2, wherein the backing material has an elongation of less than 250% at a load of 10 N/cm.

7. Backing material according to claim 1 or 2, wherein the backing material has an ultimate tensile stress elongation of less than 40%.

8. Backing material according to claim 1 or 2, wherein the backing material has a basis weight of less than 350 g/m$^2$.

9. Backing material according to claim 1 or 2, wherein the backing material is tearable by hand perpendicular to the orientation of the stitches in the direction of the stitches, or both.

10. Backing material according to claim 1 or 2, wherein the fibres used to form the web have a water retention capacity of more than 0.5%.

11. Backing material according to claim 1 or 2, wherein the backing material is reinforced with one or more monofil, multifil, staple fibre or spun fibre yarns; with oriented high-strength fibres, or a combination thereof the yarns, fibres or both having a strength of at least 40 cN/tex.

12. Backing material according to claim 11, wherein the backing material can be torn by hand perpendicular to the orientation of the reinforcement in the direction of the reinforcement or both.

13. Backing material according to claim 1, wherein the self-adhesive composition has a dynamic-complex glass transition temperature at a frequency of 0.1 rad/s of less than 5° C.

14. Backing material according to claim 1, wherein the yarns have a moisture absorption of less than 30%.

15. Backing material according to claim 1, wherein the self-adhesive composition is a hot-melt adhesive composition.

16. Backing material according to claim 15, wherein the hot-melt adhesive composition is based on A-B or A-B-A block copolymers, or mixtures thereof, where phase A is principally polystyrene or its derivatives and phase B is ethylene, propylene, butylene, butadiene, isoprene or mixtures thereof.

17. Backing material according to claim 15, wherein the hot-melt adhesive composition consists of
from 10% by weight to 90% by weight of block copolymers,
from 5% by weight to 80% by weight of tackifiers, less than 60% by weight of plasticizers,
less than 15% by weight of additives, and
less than 5% by weight of stabilizers.

18. Backing material according to claim 15, wherein the hot-melt adhesive composition is applied by halftone printing, thermal screen printing or intaglio printing.

19. Backing material according to claim 15, wherein the hot-melt adhesive composition is applied in the form of polygeometric domes to the backing material.

20. Backing material according to claim 15, wherein the hot-melt adhesive composition is coated on the backing material with a weight per unit area of greater than 15 g/m².

21. Backing material according to claim 15, wherein the hot-melt adhesive composition is foamed.

22. Backing material according to claim 1, wherein the coated backing material has an air permeability of greater than 1 cm³/(cm²*s), or a water vapour permeability of greater than 500 g/(m²*24 h) or both.

23. Backing material according to claim 1, wherein on the side opposite that coated with the self-adhesive composition, the backing material is finished with a water-repellent layer, impregnation, release layer or coating.

24. Backing material according to claim 1, wherein at least one additional layer comprising sheets, foams or nonwovens is applied on the backing material.

25. Backing material according to claim 1, wherein the coated backing material is covered after application of the self-adhesive composition or is provided with a wound pad or with padding.

26. Backing material according to claim 1, wherein the backing material is coated with metallic substances by vapor deposition.

27. Backing material according to claim 1, wherein the coated backing material is sterilizable by γ (gamma) radiation.

28. An improved method for orthopedic or phlebological bandaging or dressing wherein the improvement comprises providing a bandage having a backing material having a nonwoven web overstitched by yarns, wherein the ultimate tensile stress strength of the backing material is at least 30 N/cm and the backing material is coated partially or over its full area on at least one side with a self-adhesive composition.

29. The method according to claim 28, wherein the yarns have a moisture absorption of less than 30%.

30. An improved method for orthopedic or phlebological bandaging or dressing wherein the improvement comprises providing a bandage having a backing material having a nonwoven web which is reinforced by the formation of stitches formed by loops from the fibers of the web, the number of stitches on the web being at least 5/cm, and wherein the ultimate tensile stress strength of the backing material is at least 30 N/cm, and the backing material is coated partially or over its full area on at least one side with a self-adhesive composition.

31. The method according to claim 30, wherein the number of stitches on the web is at least 5/cm.

32. The method according to claim 3, wherein the backing material generates a compression force of from 0.2 N/cm to 10 N/cm at an elongation of from 20% to 70%.

33. The method according to claim 28 or 30, wherein the webs have longitudinal stitches.

34. The method according to claim 28 or 30, wherein the backing material has an elongation of less than 250% at a load of 10 N/cm.

35. The method according to claim 28 or 30, wherein the backing material has an ultimate tensile stress elongation of less than 40%.

36. The method according to claim 28 or 30, wherein the backing material has a basis weight of less than 350 g/m².

37. The method according to claim 28 or 30, wherein the backing material is tearable by hand perpendicular to the orientation of the stitches, in the direction of the stitches, or both.

38. The method according to claim 28 or 30, wherein the fibres used to form the web have a water retention capacity of more than 0.5%.

39. The method according to claim 28 or 30, wherein the backing material is reinforced with one or more monofil, multifil, staple fibre or spun fibre yarns; with oriented high-strength fibres, or a combination thereof the yarns, fibres or both having a strength of at least 40 cN/tex.

40. The method according to claim 39, wherein the backing material can be torn by hand perpendicular to the orientation of the reinforcement, in the direction of the reinforcement or both.

41. The method according to claim 28, wherein the self-adhesive composition has a dynamic-complex glass transition temperature at a frequency of 0.1 rad/s of less than 5° C.

42. The method according to claim 28, wherein the self-adhesive composition is a hot-melt adhesive composition.

43. The method according to claim 42, wherein the hot-melt adhesive composition is based on A-B or A-B-A block copolymers, or mixtures thereof, where phase A is principally polystyrene or its derivatives and phase B is ethylene, propylene, butylene, butadiene, isoprene or mixtures thereof.

44. The method according to claim 42, wherein the hot-melt adhesive composition consists of
from 10% by weight to 90% by weight of block copolymers,
from 5% by weight to 80% by weight of tackifiers,
less than 60% by weight of plasticizers,
less than 15% by weight of additives, and
less than 5% by weight of stabilizers.

45. The method according to claim 42, wherein the hot-melt adhesive composition is applied by halftone printing, thermal screen printing or intaglio printing.

46. The method according to claim 42, wherein the hot-melt adhesive composition is applied in the form of polygeometric domes to the backing material.

47. The method according to claim 42, wherein the hot-melt adhesive composition is coated on the backing material with a weight per unit area of greater than 15 g/m².

48. The method according to claim 42, wherein the hot-melt adhesive composition is foamed.

49. The method according to claim 28, wherein the coated backing material has an air permeability of greater than 1 $cm^3/(cm^{2*}s)$, or a water vapour permeability of greater than 500 $g/(m^{2*}24\ h)$ or both.

50. The method according to claim 28, wherein on the side opposite that coated with the self-adhesive composition, the backing material is finished with a water-repellent layer, impregnation, release layer or coating.

51. The method according to claim 28, wherein at least one additional layer comprising sheets, foams or nonwovens is applied on the backing material.

52. The method according to claim 28, wherein the coated backing material is covered after application of the self-adhesive composition or is provided with a wound pad or with padding.

53. The method according to claim 28, wherein the backing material is coated with metallic substances by vapour deposition.

54. The method according to claim 28, wherein the coated backing material is sterilizable by γ (gamma) radiation.

* * * * *